US010552578B2

(12) United States Patent
Jacobs et al.

(10) Patent No.: US 10,552,578 B2
(45) Date of Patent: Feb. 4, 2020

(54) PACKAGE LOCATING SYSTEM

(71) Applicant: PerceptiMed, Inc., Mountain View, CA (US)

(72) Inventors: Alan Jeffrey Jacobs, Palo Alto, CA (US); Darius Mostowfi, San Carlos, CA (US); Jennifer A. L. Jacobs, Mountain View, CA (US)

(73) Assignee: PerceptiMed, Inc., Mountain View, CA (US)

( * ) Notice: Subject to any disclaimer, the term of this patent is extended or adjusted under 35 U.S.C. 154(b) by 0 days.

(21) Appl. No.: 14/630,310

(22) Filed: Feb. 24, 2015

(65) Prior Publication Data

US 2015/0170097 A1 Jun. 18, 2015

Related U.S. Application Data

(63) Continuation of application No. PCT/US2013/056691, filed on Aug. 26, 2013.

(Continued)

(51) Int. Cl.
*G06F 19/00* (2018.01)
*G06Q 50/22* (2018.01)
(Continued)

(52) U.S. Cl.
CPC ............ *G06F 19/3456* (2013.01); *A61J 1/03* (2013.01); *B65D 25/20* (2013.01); *B65D 33/06* (2013.01);
(Continued)

(58) Field of Classification Search
CPC ............... G06F 19/3462; G06F 19/326; G06F 19/3456; G06F 21/31; G06K 2017/0045;
(Continued)

(56) References Cited

U.S. PATENT DOCUMENTS 6,088,856 A * 7/2000 Boyer ...................... A47G 9/10
5/639
6,972,682 B2 12/2005 Lareau et al.
(Continued)

FOREIGN PATENT DOCUMENTS

| CN | 1701327 A | 11/2005 |
|---|---|---|
| CN | 101568909 | 10/2009 |

(Continued)

OTHER PUBLICATIONS

PCT International Search Report and Written Opinion, PCT Application No. PCT/US13/56690, dated Dec. 16, 2013, 13 pages.
(Continued)

*Primary Examiner* — Florian M Zeender
*Assistant Examiner* — Milena Racic
(74) *Attorney, Agent, or Firm* — Fenwick & West LLP

(57) ABSTRACT

A prescription management system receives prescription information and manages containers filled with the prescription. The prescription is stored in the container and the container is attached to a tracking device storing prescription information. The tracking device is managed by the prescription management system. The tracking device is self-powered and activates an indicator when it receives a request from the prescription management system identifying the tracking device. The indicator permits a user, such as a pharmacist, to locate a desired prescription.

21 Claims, 8 Drawing Sheets

Related U.S. Application Data

(60) Provisional application No. 61/864,451, filed on Aug. 9, 2013, provisional application No. 61/772,761, filed on Mar. 5, 2013, provisional application No. 61/693,237, filed on Aug. 24, 2012.

(51) Int. Cl.

| | | |
|---|---|---|
| *G06Q 50/24* | (2012.01) | |
| *G06Q 20/20* | (2012.01) | |
| *G06Q 30/06* | (2012.01) | |
| *A61J 1/03* | (2006.01) | |
| *B65D 25/20* | (2006.01) | |
| *B65D 33/06* | (2006.01) | |
| *B65D 33/16* | (2006.01) | |
| *B65D 55/02* | (2006.01) | |
| *G06Q 10/08* | (2012.01) | |

(52) U.S. Cl.
CPC .......... *B65D 33/16* (2013.01); *B65D 55/02* (2013.01); *G06Q 10/0833* (2013.01); *G06Q 20/20* (2013.01); *G06Q 30/0637* (2013.01); *G06Q 50/22* (2013.01); *G06Q 50/24* (2013.01)

(58) Field of Classification Search
CPC .. G06K 7/0008; G06K 7/10475; G06Q 10/08; G07F 17/0092; G07F 11/62
USPC ........ 5/654, 639, 644; 705/22, 2, 3; 235/375
See application file for complete search history.

(56) References Cited

U.S. PATENT DOCUMENTS

| | | | |
|---|---|---|---|
| 7,053,753 B2 | 5/2006 | Kacalek et al. | |
| 7,496,521 B1 | 2/2009 | Louie et al. | |
| 8,113,438 B1 | 2/2012 | Leason et al. | |
| 8,306,651 B2* | 11/2012 | Chudy | A47B 63/062 700/215 |
| 2002/0104848 A1* | 8/2002 | Burrows | A61J 7/0481 221/1 |
| 2002/0169635 A1 | 11/2002 | Shillingburg | |
| 2004/0064215 A1 | 4/2004 | Greeven et al. | |
| 2004/0124988 A1 | 7/2004 | Leonard et al. | |
| 2005/0098626 A1 | 5/2005 | Jordan et al. | |
| 2005/0253703 A1 | 11/2005 | He et al. | |
| 2006/0265102 A1 | 11/2006 | Bain | |
| 2007/0023512 A1 | 2/2007 | Miller et al. | |
| 2007/0188306 A1 | 8/2007 | Tethrake et al. | |
| 2007/0204497 A1* | 9/2007 | de la Huerga | G06F 19/3462 40/630 |
| 2008/0035520 A1 | 2/2008 | Caracciolo | |
| 2008/0218358 A1 | 9/2008 | Derrick et al. | |
| 2009/0037575 A1 | 2/2009 | Crystal et al. | |
| 2009/0230189 A1* | 9/2009 | Louie | G06F 19/327 235/385 |
| 2009/0230778 A1 | 9/2009 | Alfven et al. | |
| 2009/0322510 A1 | 12/2009 | Berger et al. | |
| 2010/0007464 A1 | 1/2010 | McTigue | |
| 2010/0030371 A1 | 2/2010 | Chudy et al. | |
| 2010/0049635 A1 | 2/2010 | Delaney et al. | |
| 2010/0238039 A1 | 9/2010 | Tethrake et al. | |
| 2011/0054668 A1 | 3/2011 | Holmes et al. | |
| 2011/0060457 A1* | 3/2011 | De Vrught | A61J 1/03 770/241 |
| 2011/0068906 A1* | 3/2011 | Shafer | G06K 7/0008 340/10.3 |
| 2011/0131096 A1 | 6/2011 | Frew et al. | |
| 2011/0279245 A1 | 11/2011 | Hynes et al. | |
| 2012/0056000 A1 | 3/2012 | Shores | |
| 2013/0253700 A1 | 9/2013 | Carson et al. | |
| 2013/0297325 A1* | 11/2013 | Cobb | G06Q 50/22 705/2 |
| 2015/0169843 A1 | 6/2015 | Jacobs et al. | |
| 2016/0110518 A1 | 4/2016 | Louie et al. | |
| 2017/0053099 A1 | 2/2017 | Coughlin et al. | |
| 2017/0076063 A1 | 3/2017 | Louie et al. | |
| 2018/0032680 A1 | 2/2018 | Chen et al. | |

FOREIGN PATENT DOCUMENTS

| | | |
|---|---|---|
| CN | 101918949 A | 12/2010 |
| CN | 102473255 A | 5/2012 |
| JP | S 61-155106 A | 7/1986 |
| JP | H05-128376 A | 5/1993 |
| JP | H06-271023 A | 9/1994 |
| JP | H07-247009 A | 9/1995 |
| JP | 3024113 U | 5/1996 |
| JP | 2000-204810 A | 7/2000 |
| JP | 2002-019928 A | 1/2002 |
| JP | 2002-092165 A | 3/2002 |
| JP | 2003-507819 A | 2/2003 |
| JP | 2004-065986 A | 3/2004 |
| JP | 2004-148120 A | 5/2004 |
| JP | 2006-004119 A | 1/2006 |
| JP | 2006-209287 A | 8/2006 |
| JP | 2010-500128 A | 1/2010 |
| JP | 2010-023952 A | 2/2010 |
| JP | 2013-529095 A | 7/2013 |
| WO | WO 01/15006 A1 | 3/2001 |
| WO | WO 2011/112606 A1 | 9/2011 |
| WO | WO 2013/112591 A1 | 8/2013 |

OTHER PUBLICATIONS

PCT Invitation to Pay Additional Fees, PCT Application No. PCT/US13/56691, dated Dec. 5, 2013, 2 pages.
PCT International Search Report and Written Opinion, PCT Application No. PCT/US13/56691, dated Jan. 31, 2014, 24 pages.
United States Office Action, U.S. Appl. No. 14/630,306, dated Jun. 23, 2015, 16 pages.
United States Office Action, U.S. Appl. No. 14/630,306, dated Mar. 4, 2016, 19 pages.
United States Office Action, U.S. Appl. No. 14/630,306, dated Sep. 27, 2016, 17 pages.
Canadian Office Action, Canadian Application No. 2,882,273, dated May 12, 2016, 3 pages.
Canadian Office Action, Canadian Application No. 2,882,271, dated May 30, 2016, 4 pages.
Japanese First Office Action, Japanese Application No. 2015-528715, dated Sep. 19, 2017, 6 pages.
Canadian Second Office Action, Canadian Application No. 2,882,273, dated Apr. 4, 2017, 6 pages.
Canadian Second Office Action, Canadian Application No. 2,882,271, dated May 15, 2017, 4 pages.
Chinese First Office Action, Chinese Application No. 201380055791.1, dated Oct. 8, 2016, 22 pages.
Chinese Second Office Action, Chinese Application No. 201380055791.1, dated May 31, 2017, 20 pages.
Chinese First Office Action, Chinese Application No. 201380055767.8, dated Jun. 1, 2017, 27 pages.
Japanese First Office Action, Japanese Application No. 2015-528716, dated Jul. 25, 2017, 6 pages.
United States Office Action, U.S. Appl. No. 14/630,306, May 2, 2017, 18 pages.
Australian Second Examination Report, Australian Application No. 2013305512, dated Aug. 13, 2018, 3 pages.
Chinese Third Office Action, Chinese Application No. 201380055767.8, dated Aug. 20, 2018, 28 pages.
PCT International Search Report and Written Opinion, PCT Application No. PCT/US18/40131, dated Sep. 6, 2018, 15 pages.
PCT International Search Report and Written Opinion, PCT Application No. PCT/US2018/040136, dated Sep. 14, 2018, 13 pages.
Australian First Examination Report, Australian Application No. 2013305512, dated Jan. 15, 2018, 3 pages.
Australian First Examination Report, Australian Application No. 2013305511, dated Jan. 22, 2018, 3 pages.
Australian Second Examination Report, Australian Application No. 2013305511, dated Jul. 12, 2018, 3 pages.

(56) References Cited

OTHER PUBLICATIONS

Canadian Third Office Action, Canadian Application No. 2,882,273, dated Apr. 4, 2018, 4 pages.
Canadian Third Office Action, Canadian Application No. 2,882,271, dated May 3, 2018, 4 pages.
Chinese Second Office Action, Chinese Application No. 201380055767.8, dated Nov. 24, 2017, 31 pages.
Chinese Third Office Action, Chinese Application No. 201380055791.1, dated Nov. 30, 2017, 16 pages.
Chinese Fourth Office Action, Chinese Application No. 201380055791.1, dated Jun. 4, 2018, 17 pages.
Japanese Office Action, Japanese Application No. 2015-528715, dated May 29, 2018, 11 pages.
Lebhar-Friedman, Inc., "Hi-School to pioneer test of will-call prescription-tracking system," Drug Store News, vol. 25, Iss. 10, Aug. 18, 2003, pp. 1-3.
United States Office Action, U.S. Appl. No. 14/630,306, dated Jun. 25, 2019, 21 pages.

* cited by examiner

PACKAGE LOCATING SYSTEM

CROSS REFERENCE TO RELATED APPLICATIONS

This application is a continuation of PCT Application No. PCT/US2013/056691, filed Aug. 26, 2013, which claims the benefit of U.S. Provisional Application No. 61/693,237, filed Aug. 24, 2012, U.S. Provisional Application No. 61/772,761, filed Mar. 5, 2013, and U.S. Provisional Application No. 61/864,451, filed Aug. 9, 2013, each of which is incorporated by reference in its entirety.

BACKGROUND

This invention relates generally to management systems and in particular to management systems of a pharmaceutical working environment.

Pharmacies fill and deliver to customers more than 4 billion prescriptions each year in the United States. The average retail store fills 200-400 customer prescriptions each day. Customers do not necessarily pick up these prescriptions the same day they are filled. Filled prescriptions are typically held for 1-2 weeks or more before returned to stock if not picked up. The will call process and storage bins in retail pharmacies must organize and hold hundreds to thousands of filled prescriptions awaiting pickup. One of the challenges in managing this large volume of filled prescriptions includes the time a cashier spends searching the will call bins for a waiting customer's prescription. This translates into the time customers spend in line waiting to pick their prescriptions and affects customer satisfaction. Errors in filing prescriptions in the wrong bin can lead to misplaced prescriptions that must be refilled while the customer waits, or prolonged time spent searching the store for the prescription.

When customers do not pickup their prescriptions, pharmacies need to retrieve these aged prescriptions from the will call bins to return the unused medications to stock. Locating and retrieving these aged prescriptions from among the hundreds to thousands of packages in the will call bins is a time-consuming process for pharmacy staff.

More efficient and cost effect solutions are needed for the storage and retrieval of filled prescriptions in the retail pharmacy environment.

SUMMARY

A prescription management system receives prescription information and manages containers filled with the prescription. The prescription management system receives an indication from a pharmacist or a prescription filling system that a particular container is filled with a prescription. The container is stored in a pharmacy, and an indicator on the container is activated when the prescription in the desired container is required. The indicator can be an audio or visual indicator that the pharmacist can use to identify the container. Prior to dispensing the prescription to a customer, information stored on the container is verified with the prescription information at the prescription management system to ensure the correct container was retrieved.

While the prescription management system is described as managing prescription containers, the system can be used for organizations of medications outside of the pharmacy environment, such as within hospitals or nursing homes, or for organization of other items besides medications. For example, the system can be used for organizing and tracking different types of products within a store, for tracking books in a library, for tracking files in an office, for home use to track audio or video content or any other situation in which organizing, tracking and being able to quickly locate various items is beneficial.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Overview

Figure 1:
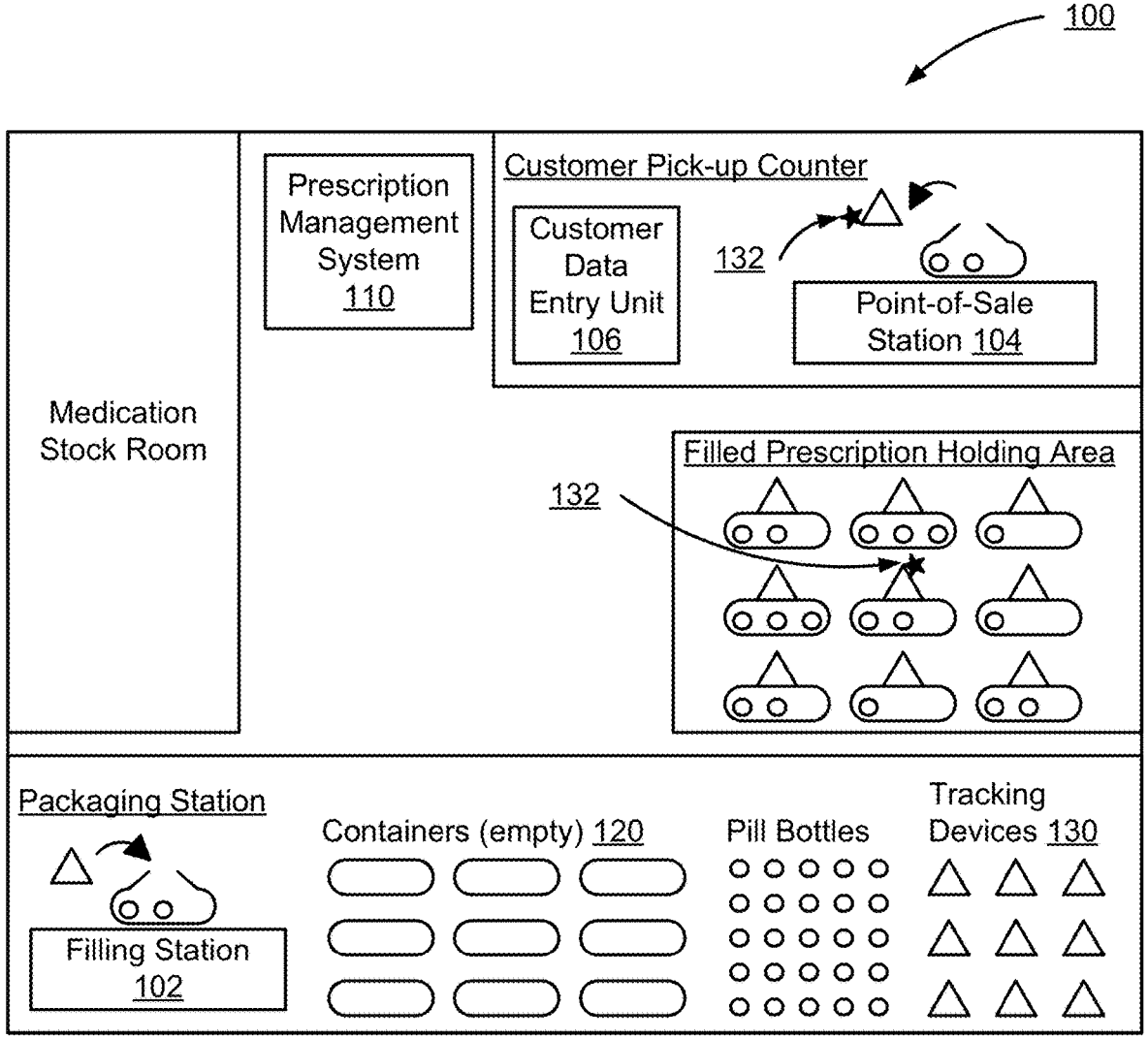
FIG. 1 shows one embodiment of a pharmaceutical environment using a prescription management system.

FIG. 1 shows one embodiment of a pharmaceutical environment 100 using a prescription management system 110. The prescription management system 110 may be a separate or combined system with other management systems, and may reside locally in the store or at a remote location. The prescription management system 110 receives prescription information and manages containers 120 filled with the prescription. The prescription management system 110 receives an indication from a pharmacist or the prescription management system 110 that a particular container 120 is filled with a prescription. The pharmacist stores the container 120 in the pharmacy and, when the prescription is ready to be dispensed to a customer, the prescription management system 110 activates an indicator 132 on the container 120. The indicator 132 is an audio, visual, or other sensory signal that is used to identify the desired container 120. In one embodiment, prior to dispensing the prescription to the customer, information stored on the container is verified with the prescription information received by the prescription management system 110 to ensure the correct container was retrieved. The pharmaceutical environment 100 includes a medication stock room, a packaging station, a filled prescription holding area and a customer pick-up counter.

The packaging station includes a filling station 102, a plurality of tracking devices 130, a plurality of pill bottles, and a plurality of empty containers 120. At the filling station 102, the plurality of empty containers 120 are filled with the pharmaceutical(s) corresponding to a prescription. The pharmaceuticals may be a pill, capsule, tablet, inhaler, injectable medication, cream, salve, and any other item prescribed to a customer. The filled containers 120 are attached to one of the plurality of tracking devices 130, such as through a clipping mechanism, adhesive, or mating components. In another embodiment, the tracking device 130 is a part of the container 120. In other embodiments, the tracking device 130 is placed in the container 120.

When the prescription is filled at the filling station 102, the filling station 102 transmits a prescription identifier and a tracking device identifier associated with the filled prescription to the prescription management system 110. The prescription management system 110 associates the tracking device identifier with the filled prescription. In one embodiment, when tracking the prescription order, the prescription management system identifies the tracking device 130 holding the prescription by looking up the tracking device identifier and comparing the tracking device identifier with the information of the associated filled prescription information.

In one embodiment, the prescription management system 110 programs the tracking device 130 to store a prescription identifier. In this embodiment, the tracking device 130 is programmable to store the prescription identifier to a local memory. In one embodiment, the tracking device is signaled to receive the prescription identifier. That is, the tracking device may be dormant, in a low power mode, or in a mode not capable of receiving the prescription identifier. In another embodiment, the signal triggers the tracking device to listen to for the prescription identifier. The tracking device may be signaled by various methods, such as a press of a switch, a specific movement such as shaking, a flash of a light, an inductive impulse, a radio frequency signal, electrical contact, or other means. The prescription identifier may include a reference number of the prescription filled in the container 120, customer information, such as a customer's name, address, date of birth, personal identification number (PIN), code of a customer loyalty card, driver's license number, credit card number, or other identifying information. In one embodiment, the tracking device 130 does not store any personally identifiable information. In other embodiments, the tracking device 130 stores information similar or identical to the identifying information on a label of the prescription order of the contents in the container 120. In additional embodiments, the container 120 is already programmed with an identifier and the prescription management system 110 stores an association of the programmed identifier of the container 120 with the customer information. Thus, the prescription management system 110 can verify the prescription order and customer by scanning the container 120.

In one embodiment, the prescription management system 110 sends additional commands to the tracking device 130 when the container 120 is filled. One additional command includes a lock command to lock the container, for embodiments where the containers 120 include locking mechanisms. In another embodiment, there is a sensor system, such as a proximity sensor or magnetic sensor, located on the container 120 that recognizes when the handles have been closed. In this embodiment, the container 120 locks as a result of the handles being closed.

The filling station 102, the point-of-sale station 104, and prescription management system 110 communicate with the tracking device 130 using a wireless communication protocol, such as the Wireless Application Protocol (WAP). In other embodiments, the prescription management system 110 communicates with the container 120 through other wireless communication protocols, including the Worldwide Interoperability for Microwave Access (WiMAX), Global System for Mobile Communications (GSM), 802.11 standards of the Wireless Local Area Network (WLAN), Wireless Personal Area Networks (WPAN), Bluetooth, or Infrared Data Association (IrDA).

In other embodiments, communication is achieved through a physical connection with the filling station 102 and the point-of-sale station 104. The physical connection can be through mounting the container 120 on a rod attached to the station, a bin attached to the station, or a power charge pad on the station.

When a container is filled, the pharmacist adds the container 120 to the filled prescription holding area. Generally, the filled prescription holding area is a rack or a plurality of will call bins. Since there are power sources in the tracking devices 130, such as an internal battery, super capacitor, or other power storage mechanism, which may be rechargeable or replaceable, the filled prescription holding area may not be connected to a power source.

In the embodiment where the power source in the tracking devices 130 is rechargeable, the tracking devices 130 can be recharged through a physical connection with the filling station 102 and the point-of-sale station 104. The physical connection can be through mounting the container 120 on a rod attached to the station, a bin attached to the station, or a power charge pad on the station, powered through conduction, through induction, or by motion. In another embodiment, the container includes a photovoltaic (solar/indoor light) component.

In one embodiment, rather than being filled at the filling station 102, the container 120 is filled with the prescription at a remote location, such as a central pharmacy, where the container 120 is filled with the prescription. The tracking device 130 may be associated with the prescription or programmed with prescription information or prescription identifier at the remote pharmacy rather than at the local pharmacy 100. In one embodiment, when the tracking device 130 arrives at the pharmacy 100, the prescription management system 110 receives a prescription identifier or a tracking device identifier from the tracking device 130. The prescription management system 110 registers the prescription as being received in the store and associates the prescription with the tracking device identifier. In one embodiment, the prescription management system 110 uses the prescription information or prescription identifier in the tracking device to identify the prescription or to add customer information relating to the prescription. This system allows remote filling of a prescription and a quick association of the tracking device within the local pharmacy 100. In the embodiment where the container 120 includes a locking mechanism, the container 120 may also be securely locked during transport.

In one embodiment, the filled prescription holding area includes a plurality of guidepost stations (not shown) placed in the filled prescription holding area. The guidepost stations include locating features, such as a visual or auditory alarm, that are activated when an indicator 132 on a nearby container 120 is activated.

The customer pick-up counter includes a customer data entry unit 106 and a point-of-sale station 104. The user receives customer data and verifies the customer at the pick-up counter is permitted to be dispensed the prescription retrieved by the user, such as a pharmacist, cashier, or worker. The user receives customer information from the customer directly, through the customer data entry unit 106, which may be a keypad, touch-screen, card reader, a register, a near-field communication device, and any other suitable device for obtaining information from a customer. In one embodiment, the prescription management system 110 sends a wireless command to the associated tracking device 130 using the prescription identifier or the tracking device identifier. The tracking device 130 activates the indicator 132 on the container 120 associated with the customer. The user identifies the container 120 containing the desired prescription using the active indicator 132, and retrieves the associated container 120 from the filled prescription holding area.

In embodiments where the tracking device 130 maintains a prescription identifier, during verification at the point-of-sale station 104, prescription information stored at the prescription management system 110 is compared through a wireless connection with the prescription identifier stored in the tracking device 130, where the prescription identifier could be stored in volatile or non-volatile memory. The user is notified of the results of the comparison and whether the container 120 selected by the user has prescription information matching the prescription information stored at the prescription management system 110. In one embodiment, the results are shown on a visual display located on the container 120, which may be a display that requires low to no power when maintaining an image, such as an electronic paper or e-paper display. In other embodiments, the results are shown on a visual display on a computer screen at the pick-up counter. This allows the user to determine whether the correct prescription was retrieved from the filled prescription holding area.

In certain embodiments, further verification is performed prior to releasing the prescription in the container 120 to the customer. At the customer data entry unit 106 in the pick-up counter, a customer enters a customer or prescription identifier for a prescription order at the customer data entry unit 106. In this embodiment, the customer's identity is verified in addition to verifying the requested prescription was retrieved from the filled prescription holding area. In one embodiment, the customer enters a customer or prescription identifier using a key pad. In other embodiments, the customer provides the prescription identifier using a magnetic stripe reader, a bar code scanner or a Near Field Communication (NFC)/Radio Frequency Identification (RFID) scanner. In other embodiments, instead of entering additional information for prescription retrieval, the customer is required to receive counseling from the user (i.e., a pharmacist or pharmacy technician) about the prescription in the container. The prescription identifier entered by the customer is compared with the prescription identifier stored in the prescription management system 110 or prescription identifier stored in the tracking device 130 of the retrieved container 120. In other embodiments, the prescription management system 120 automatically sends a command to the container 120 to activate the indicators 132 when the customer enters information in the customer data entry unit 106. In the embodiment where the container 120 is locked, when the verification of the customer from the point-of-sale station is received, an unlock command is sent to the tracking device 130 component of the container 120. In other embodiments, the customer is required to receive counseling of the prescription in the container in addition to or instead of the additional customer verification.

In other embodiments, if the verification fails, because the user retrieves the wrong container 120 or the customer enters the wrong information, the prescription management system 110 transmits a signal to cause the container 120 to emit an audible alert, visual alert, or a combination of the mentioned alerts to notify the user.

Figure 2:
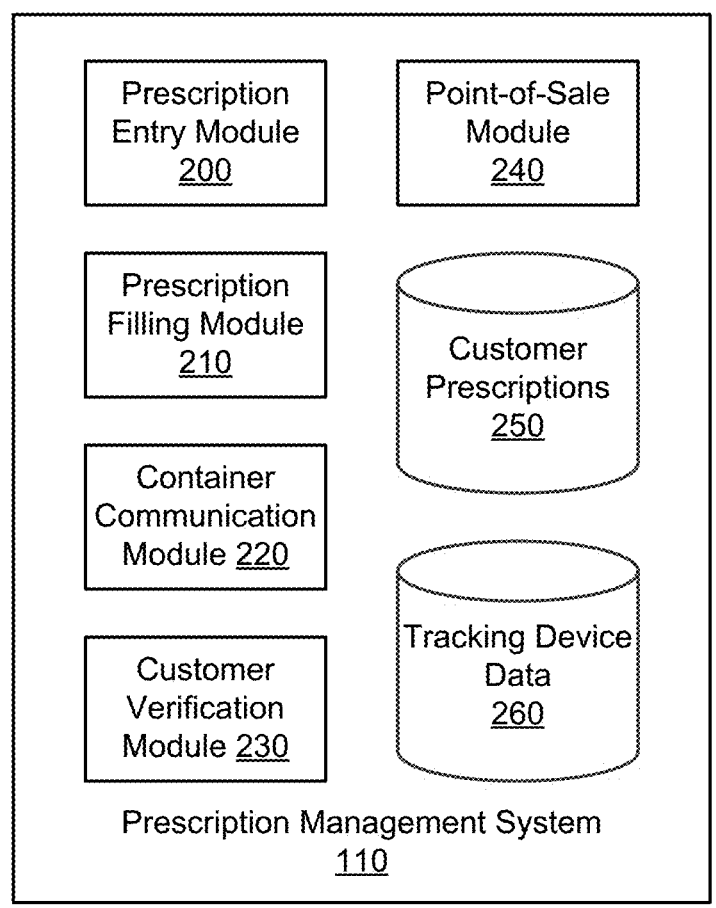
FIG. 2 illustrates components of a prescription management system, according to one embodiment

FIG. 2 illustrates components of a prescription management system 110 in one embodiment. The prescription management system 110 includes various modules, including a prescription entry module 200, a prescription filling module 210, a container communication module 220, a customer verification module 230, and a point-of-sale module 240 for managing prescription containers. During operation, the prescription management system 120 maintains various data, such as customer prescriptions 250 and tracking device data 260.

Customer prescriptions 250 stores a plurality of prescription identifiers. The prescription identifier may include a reference number of the prescription filled in the container 120, and customer information, such as a customer's name, address, date of birth, personal identification number (PIN), code of a customer loyalty card, driver's license number, credit card number, or other identifying information. In one embodiment, the tracking device 130 stores the prescription identifier. In other embodiments, the tracking device 130 has a pre-programmed identifier.

Tracking device data 260 stores a plurality of tracking device identifiers and an associated plurality of prescription information. The prescription management system 110 associates each tracking device identifier with the respective prescription order, associating each container 120 with a customer.

The prescription entry module 200 manages entry of prescriptions to the pharmacy 100. The prescription management system 110 stores the prescription order and customer information of the prescription identifier into customer prescriptions 122 or sends the information to the customer verification module 230 if the customer information is already maintained in the customer prescriptions 122. The prescription entry module 200 enters a prescription order into customer prescriptions 250 after receiving prescription information. In the embodiment where the prescription order is filled at a remote site, when the container 120 arrives at the local pharmacy 100, the prescription is received by the prescription entry module 200 by various means. In one method, the prescription entry module 200 scans prescription information on the tracking device 130 of the container 120 and queries a remote prescription management system using the prescription information. Once scanned, the prescription entry module 200 files the prescription order into the prescription management system 110. Other methods include integrating an additional management system with the local management system, allowing access to the database of the additional management system.

The prescription filling module 210 manages the prescription orders and associates a filled prescription with a tracking device 130. The prescription filling module 210 receives customer information and accesses the customer prescriptions 250 for the prescription order. Once the prescription is placed in the container 120, the prescription filling module 210 receives the tracking device identifier for the tracking device 130 attached to the container 120. The prescription filling module 210 updates the tracking device data 260 with the tracking device identifier and associated prescription information. In embodiments where the tracking device 130 is updated with prescription information, the prescription filling module 210 transmits prescription information to the tracking device 130 through the container communication module 220. In embodiments where the container 120 includes a lock, the prescription filling module 210 transmits a lock command to the tracking device 130 to lock the container 120.

The container communication module 220 relays information and commands from the prescription management system 110 to the tracking device 130 through a wireless transceiver. Once the prescription is placed in the container 120, the container communication module 220 sends the prescription information to the container 120, according to one embodiment. Other embodiments include retrieving a pre-programmed identifier of the container 120. The container communication module 116 may send commands to the container 120 including activating the indicator 132, locking the container 120 once filled, and unlocking the container 120 when retrieved by a customer. In the embodiment where the prescription identifier is stored in the tracking device 130, the container communication module 120 may also read data from the tracking device 130. To address the tracking device 130 on the wireless transceiver, the container communication module 220 transmits the tracking device identifier associated with the desired tracking device 130.

The customer verification module 230 receives a prescription identifier from the prescription entry module 200. Once the container 120 is at the point-of-sale station 104 in the customer pick-up counter, the customer verification module 230 retrieves the prescription identifier from the tracking module 130. The customer verification module 230 compares the prescription identifier with the prescription identifier received from the tracking device 130. The prescription management system 110 sends a notification to the user through a visual display indicating whether the prescription identifier matches or does not match the identifier stored on the tracking device 130. In the embodiment where the container 120 was sent a lock command, the customer verification module 230 sends an unlock command responsive to the information matching.

Figure 3:
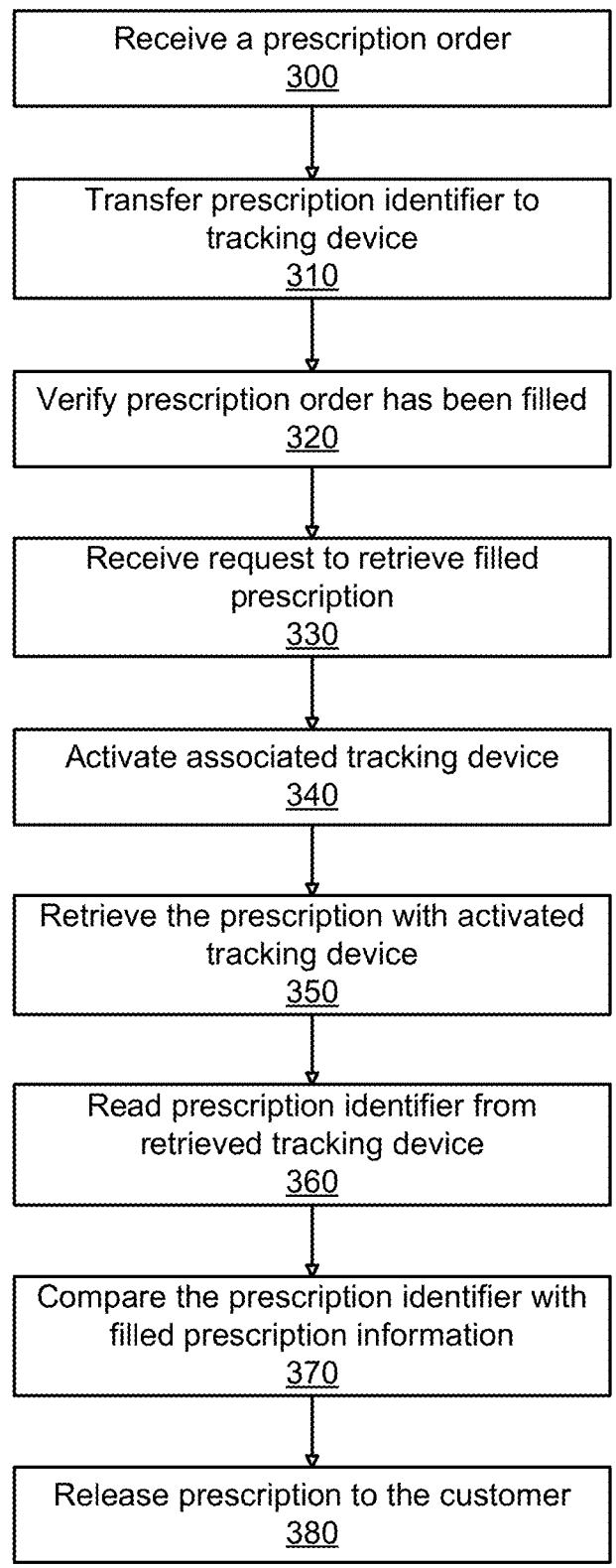
FIG. 3 is a flowchart for tracking a prescription, according to one embodiment.

FIG. 3 is a flowchart for prescription tracking according to one embodiment. This process can be performed by the various modules of the prescription management system 110. First, a prescription order is received 300. The prescription order may come from a customer, a medical practitioner, or a user, such as a pharmacy worker, cashier, or pharmacist. Once the container 120 has been filled with the associated prescription, the prescription identifier is transferred 310 to the container 120. In another embodiment, the prescription identifier includes prescription information. In one embodiment where the prescription order is filled at a remote site, the container 120 is scanned at the local pharmacy to file the prescription order in the local prescription management system 110. The prescription management system 110 optionally verifies 320 the prescription order has been filled.

Next, the prescription management system 110 receives 330 a request to retrieve a filled prescription. The prescription identifier or tracking device identifier associated with the prescription is accessed and the request to activate 340 the associated tracking device is transmitted to the tracking device 130. In one embodiment, the transmission is sent to a channel received by a plurality of the tracking devices 130. In this embodiment, the transmission specifies the prescription identifier or tracking device identifier to be activated, and the tracking devices receive the transmission and determines whether the transmission includes information designating that tracking device, by matching the information to information stored by the tracking device 130. For example, if customer Jack requests his prescription, the prescription management system 110 sends customer information associated with Jack in the activation command. In response, the tracking devices determine whether the transmitted customer information matches the stored customer information in the tracking device. The tracking devices that have customer information associated with Jack will match and activate an indicator.

After activation, a user retrieves the activated container(s) with an activated indicator. The container with the activated tracking device 130 is retrieved 350 by the user. The prescription information on the tracking device 130 is read 360. The prescription management system 110 compares 370 the prescription identifier retrieved from the tracking device with the information of the filled prescription information in the container 120. When the information matches, the user releases 380 the prescription to the customer. In other embodiments, when the information matches, the prescription management system 110 permits access to the container 120 and, in the embodiment where the container 120 is locked, the prescription management system 110 sends an unlock command to the container 120. In one embodiment, the tracking device is cleared of the prescription identifier after the information matches.

Figure 4:
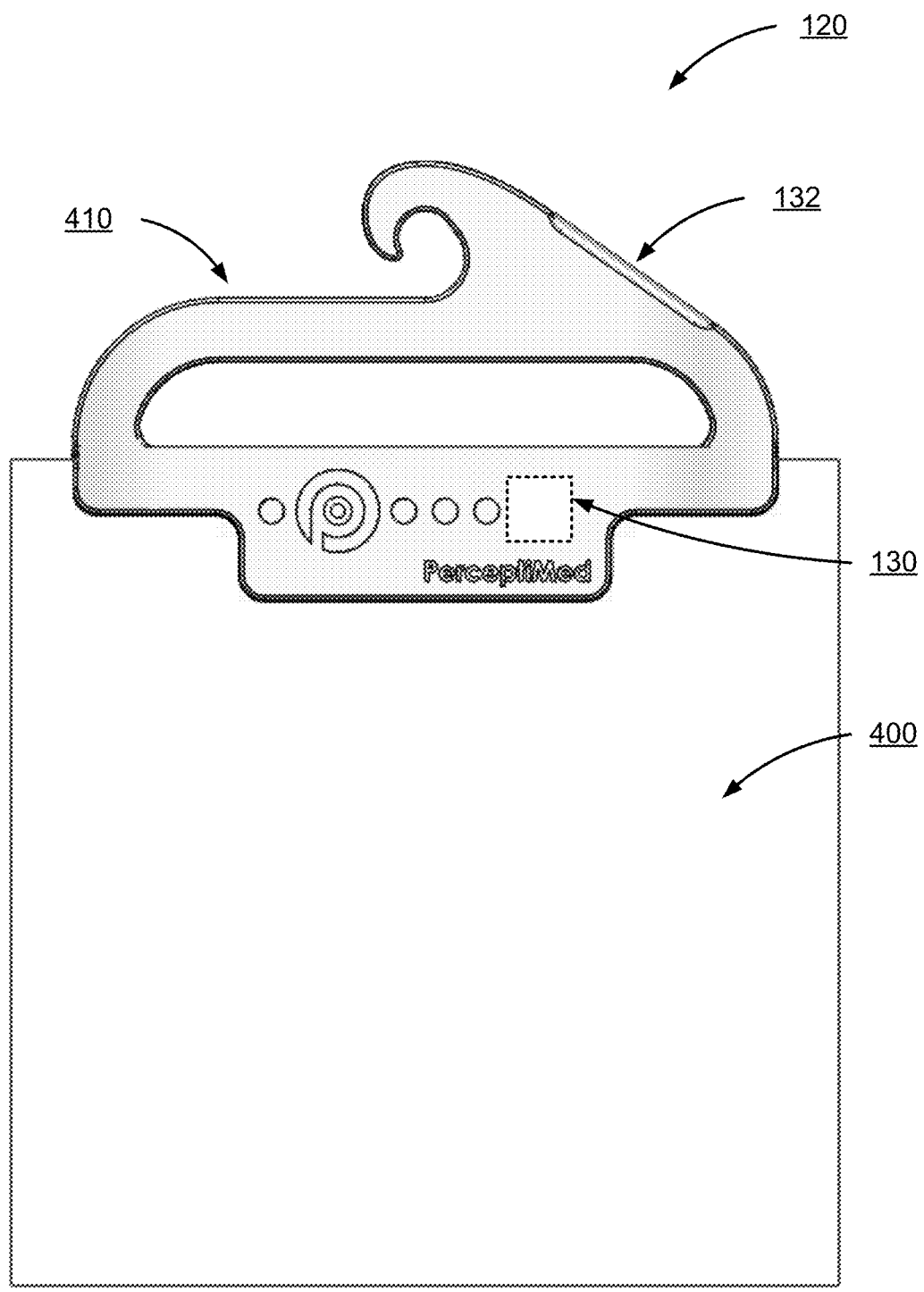
FIG. 4 is one embodiment of a container for holding prescriptions, according to one embodiment.

FIG. 4 is one embodiment of the container 120 for holding prescriptions. The container 120 includes a tracking device 130, an indicator 132, a bag 400, and a handle 410. In this embodiment, the indicator 132 is a visual indicator, e.g., a light emitting diode (LED), which lights a portion of the handle when activated. In other embodiments, the indicator 132 can be alternative visual indicators including multicolor LEDs or other visual displays, auditory indicators including speakers or buzzers, or any other component that sends a sensory cue.

In the embodiment shown in FIG. 2, the bag 400 is a clear plastic bag. In other embodiments, the bag 204 can be made of other durable, reusable materials. Alternatively, the bag 400 may be opaque rather than clear, to prevent light contamination of the prescription and view of the prescription by unauthorized persons. The handle 410 is made of two mating sides that are detachable from one another. In embodiments where the handle 410 is a clip mechanism, the two mating sides may or may not be detachable from another, depending on the hinge of the clip mechanism. The bag 400 has an open side that is attached to the mating sides of the handle 410. When the mating sides of the handle are mated with one another, the bag 400 is closed and, in other embodiments, is locked. In the embodiment shown in FIG. 4, the handle 410 comprises a hook shape with a grip area. In other embodiments, the handle 410 does not have a hook or grip.

Figure 8:
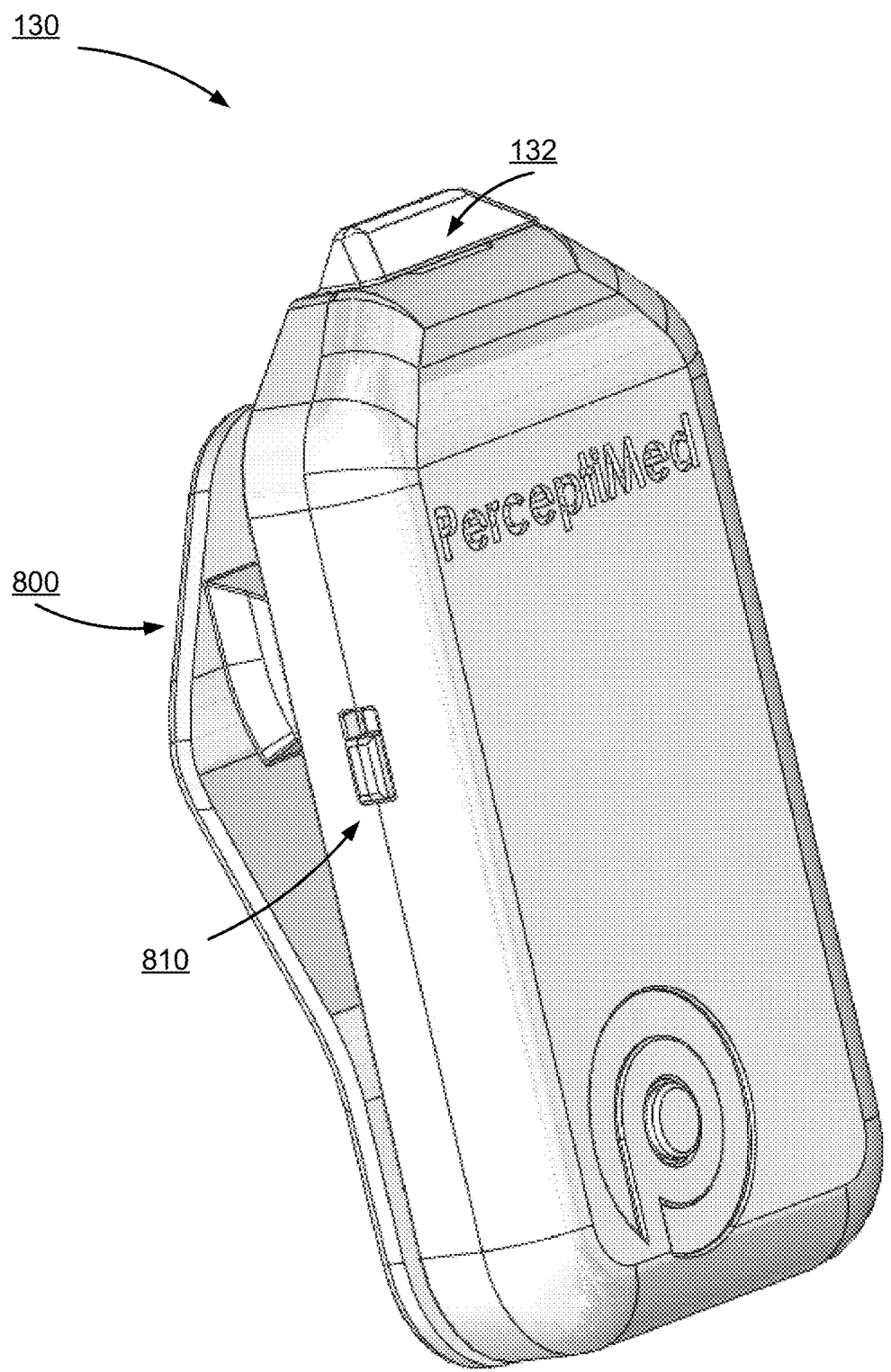
FIG. 8 shows a detachable tracking device, according to one embodiment.

In the embodiment shown in FIG. 4, the tracking device 130 is enclosed within the handle 410. In other embodiments, the tracking device 130 may be a detachable or mountable component. In other embodiments, the tracking device 130 and locking mechanism are mechanically integrated into one component. One embodiment of a detachable tracking device 130 is shown in FIG. 8.

In one embodiment, the container 120 includes additional components not shown in FIG. 4. Such components include a locking closure mechanism, a motor that controls the locking closure mechanism, a display panel, a tracking device identifier and a station connector. The motor that controls the locking closure mechanism drives the mechanical mechanism for locking and unlocking the container 120. In one embodiment, the tracking device identifier is a fixed code assigned to each container 120, such as a RFID tag. The display panel is a low-power-consumption or no-power-consumption display, such as an e-paper display, and shows the prescription identifier stored on the tracking device 130.

Figure 5:
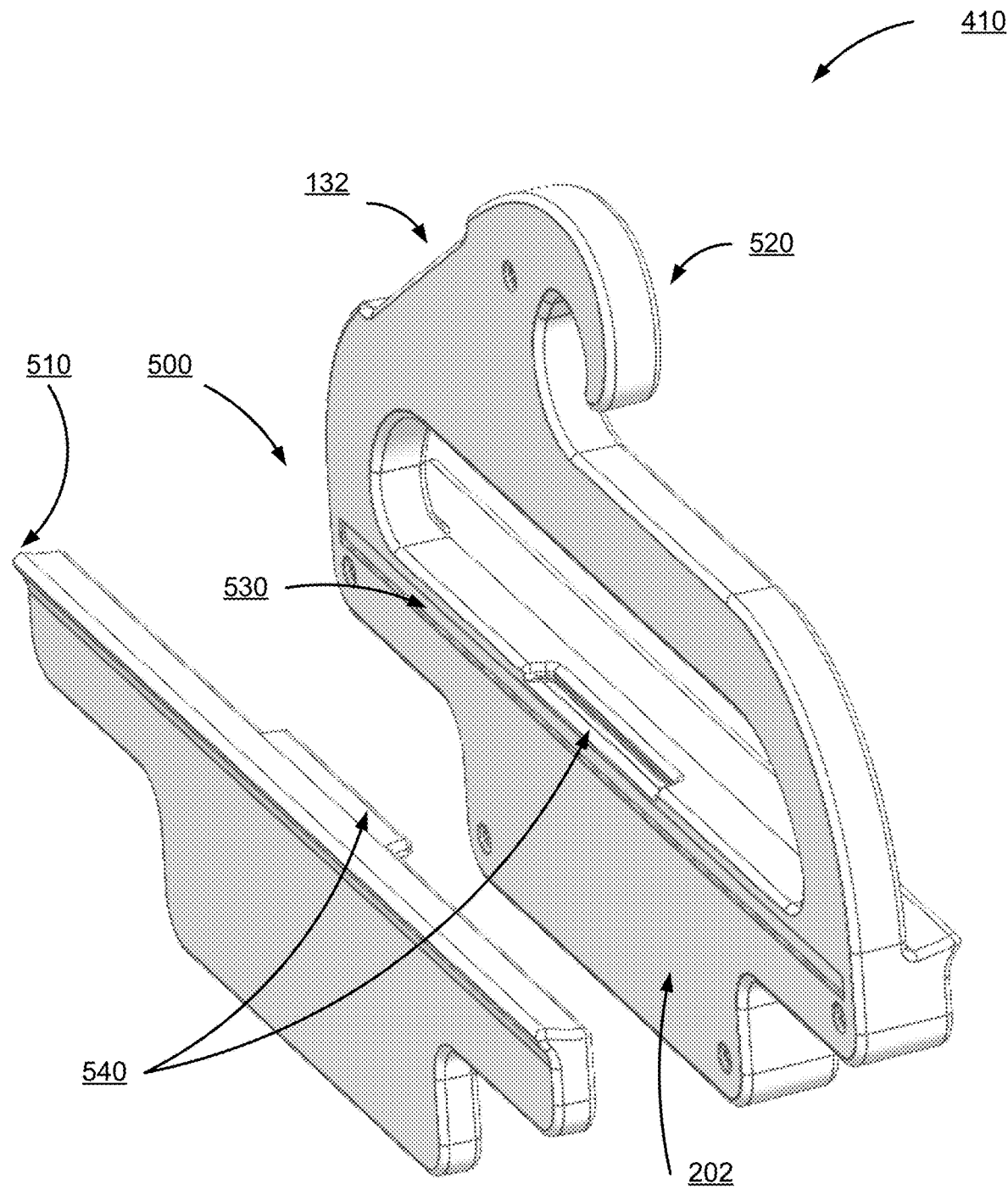
FIG. 5 is a perspective view of components of a handle for a prescription container, according to one embodiment.

FIG. 5 is a perspective view of the handle 410 according to the embodiment shown in FIG. 4. In one embodiment, the handle 410 includes a main closure mate 500 and a complementary closure mate 510, a hook 520, one or more indicator sources 132, a coupling groove 530, and a closure mechanism 540.

In one embodiment, the handle 410 includes a hook 520 in a curved C-shape. In other embodiments, the hook 520 has alternative forms, such as a T-shape, O-shape or an oval opening.

The main closure mate 500 and complementary closure mate 510 attach to the open ends of the bag 400 at the coupling groove 530 and close the open ends of the bag 400 when the mates are joined.

The handle 410 has the coupling groove 530, which is an indentation along the handle 206. The coupling groove 304 couples the bag 204 to the handle 410 using adhesives lined along the coupling groove 304, attached to the open ends of the bag 400. In other embodiments, other attachments join the bag to the coupling groove 304, such as a hook-and-loop connection, buttons, matching male and female mates, a zipper, or any other means to create a connection. In alternatives, the bag is joined to each mate using structures other than the coupling groove 530, including slide joints, twist joints or other mechanical connection joints.

The handle 410 is closed at least in part by the closure mechanism 540. In the embodiment shown in FIG. 5, the closure mechanism 540 comprises a lip located on the complementary closure mate 510 and a lip hook on the main closure mate 500. The closure in this embodiment joins the closure mates and prevents the complementary closure mate from sliding downward relative to the main closure mate (which is typically suspended by the hook). In other embodiments, the closure mechanism 540 is a Velcro connection, a plurality of one or more buttons, a plurality of one or more matching male and female mates, a zipper, a magnet, or any other means to join the closure mates.

Figure 6:
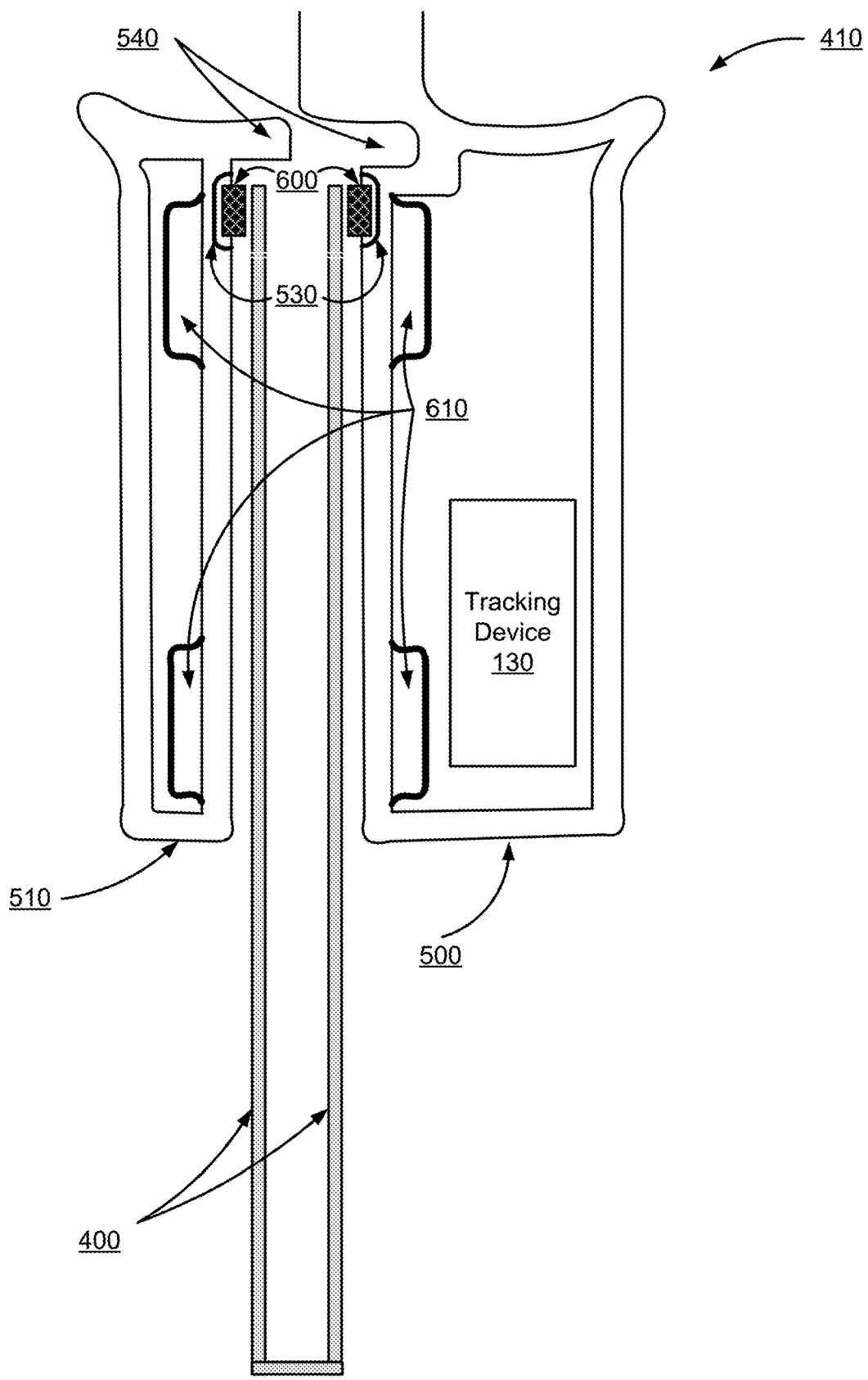
FIG. 6 is a cross-section view of a handle for a prescription container, according to one embodiment.

FIG. 6 is a cross-section view of the main closure mate 500 and the complementary closure mate 510 shown in the embodiment in FIG. 4. A set of adhesives 600 fit into the indentation of the coupling groove 530 and couples the open ends of the bag 400 with the main closure mate 500 and complementary closure mate 510. In addition to the closure mechanism 540, additional force for closing the bag 400 is provided by two sets of complementary magnets 610 enclosed in the closure mates 500, 510. The magnets 610 and closure mechanism 540 maintain the bag 400 in a closed state and prevent the closure mates from leaving contact with one another. In this embodiment, the tracking device 130 is stored in the main closure mate 500.

While described with respect to certain embodiments, the handle 410 in additional embodiments has variations. For example, the closure mechanisms may include different closures, such as snaps, mating plastic inserts, hook-and-loop structures, and various other connections. In addition, while the main closure mate 500 and the complementary closure mate 510 are shown herein as disproportionate in size, the size of each closure mate may be equal, or the complementary closure mate 510 may be larger than the main closure mate 500. Likewise, while the closure has been shown here at the base of the handle, the closure in certain embodiments may be located at the top of the handle, such as near the hook. In addition, while the closure has been shown as a connection of the inside facing sides of the closure mates, the closure in other embodiments is through closure mechanisms connected to the outside facing sides of the closure mates, such as a grip clip, strap, slide clips or other clipping mechanisms.

Figure 7:
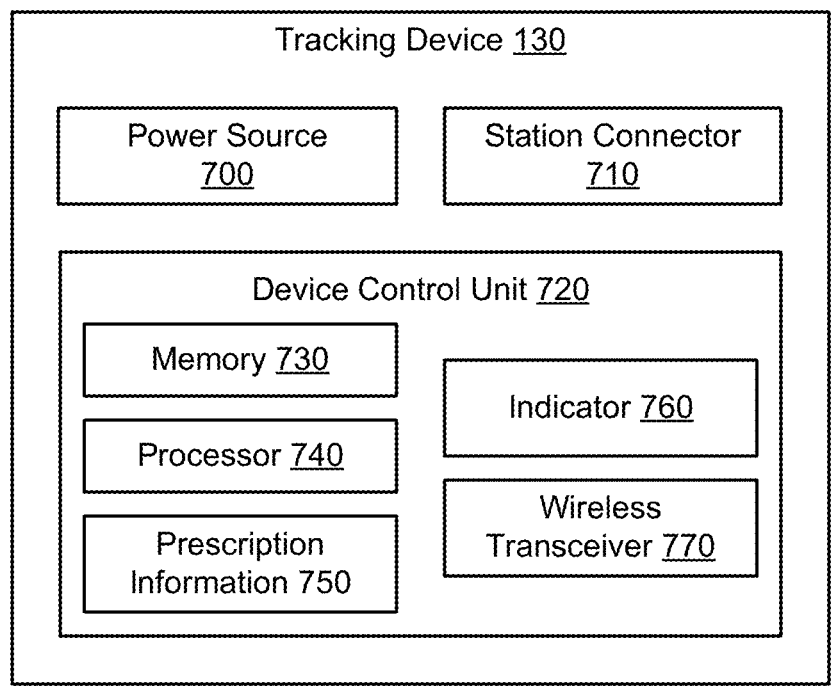
FIG. 7 is a block diagram of a tracking device, according to one embodiment.

FIG. 7 is a block diagram of a tracking device 130 according to one embodiment. The tracking device 130 may be enclosed within a container 120 or may be attachable or mountable to the container 120. The tracking device 130 includes a power source 700, a station connector 710, and a device control unit 720. The power source 700 can be an internal battery, super capacitor, or other power storage mechanism, which may be rechargeable or replaceable. In the embodiment of a rechargeable power source 700, the tracking device 130 can be recharged by coupling with the container 120 with the filling station 102 or the point-of-sale station 104 through a station connector 710. The station connector 710 can be a physical connector mounting the container 120 on a rod attached to the station, a bin attached to the station, or a power charge pad attached to the station, powered through conduction, through induction or by motion. In another embodiment, the container is powered by a photovoltaic (solar/indoor light) component.

The device control unit 720 includes a memory 730, a processor 740, at least one indicator 760, and a wireless transceiver 770. The memory 730 stores instructions and data that may be executed by the processor 740. In one embodiment, the memory 730 stores identifiers as well. Memory 730 may be a dynamic random access memory (DRAM) device, a static random access memory (SRAM) device, Flash RAM or other non-volatile storage device, combinations of the above, or some other memory device known in the art. In one embodiment, the at least one indicator 760 includes an LED indicator. In other embodiments, the indicator 760 can be other visual indicators including multicolor LEDs, visual displays, etc., auditory indicators including speakers, buzzers, etc., or any other component that sends a sensory cue. In one embodiment, the wireless transceiver 770 is the method of communication with the prescription management system 110. Other wireless communication protocol embodiments the Worldwide Interoperability for Microwave Access (WiMAX), Global System for Mobile Communications (GSM), 802.11 standards of the Wireless Local Area Network (WLAN), Wireless Personal Area Networks (WPAN), Bluetooth, or Infrared Data Association (IrDA). In one embodiment, the device control unit 720 includes a locking mechanism. Thus, in the embodiments where the container 120 includes the locking mechanism, the prescription management system 110 sends a lock command to the device control unit 720. Additional embodiments include a low-power-state feature. This feature allows the containers 120 to remain in a low-power state and require low to no power when stored away and not actively communicating with the prescription management system 110. In one embodiment, the tracking device is signaled to receive or transmit by the press of a switch, a specific movement such as a shaking, a flash of a light, inductive impulse, radio frequency signal, electrical contact, or other such method for activation. The activation signals the tracking device 130 to receive an identifier for storage.

In the embodiment where the containers 120 include locking mechanisms, the complementary components for the locking mechanism would be located on the main closure mate and complementary closure mate of the container handles (not shown). In one embodiment, the lock mechanism would be an electric lock using magnets, also known as a magnetic lock where the prescription management system 110 would actuate the lock by either supplying or removing power. In other embodiments, the electric lock mechanism would use solenoids or motors where the prescription management system 110 would actuate the lock by either supplying or removing power. Other embodiments of lock mechanisms include the prescription management system 110 reading a Radio Frequency Identification (RFID), requiring a numerical keypad, reading a security token swipe, scanning fingerprints or retinas, and identifying voiceprints. Additional embodiments include the user informing or counseling the customer of the prescription in the container 120. Other embodiments include having the user request additional verification information from the customer, such as a customer's name, address, date of birth, personal identification number (PIN), code of a customer loyalty card, driver's license number, credit card number, an answer to a private security question, or other identifying information.

In the embodiment where the containers 120 include locking mechanisms, the indicator 132 on the container 120 can be a multicolor LED that indicates the status of the lock through the color of the multicolor LED. For example, a locked container may have the multicolor LED flash red and an unlocked container may have the multicolor LED flash green. In additional embodiments, the electronic lock requires low or no power when locked.

In other embodiments, the prescription management system 110 programs the tracking device 130 through the device control unit 720 to store a prescription identifier. In this embodiment, the tracking device 130 is programmable, where information or identifiers can be stored on or removed from local memory 730. In other embodiments, the prescription management system 110 retrieves a pre-programmed identifier on the tracking device 130 through the device control unit 720. In one embodiment, the prescription identifier includes personally identifiable information. In another embodiment, the prescription identifier does not include personally identifiable information but stores information similar or identical to the identifying information on a label of the contents or the prescription order in the container 120.

In other embodiments, the device control unit 720 receives commands from the prescription management system 110 to activate the indicator signals on the container 120 and sends commands to the indicator signals to activate. The indicator signals include visual indicators, such as a LED, which lights a portion of the handle when activated. In other embodiments, the indicator signals can be visual indicators including multicolor LEDs or other visual displays, auditory indicators including speakers or buzzers, or any other component that sends a sensory cue.

FIG. 8 shows one embodiment of a detachable tracking device 130. The detachable tracking device 130 includes a power source 700 and a device control unit 720 as described above. The detachable tracking device 130 includes an attachment mechanism 800 in the form of a clip for attaching to a container 120. In one embodiment the clip of the detachable tracking device 130 includes a sticky, adhesive, or high-friction surface to prevent the clip from sliding off a container or other object attached by the clip. In one embodiment, the detachable tracking device includes a hook in a curved C-shape. In other embodiments, the hook has alternative forms, such as a T-shape, O-shape, or an oval. In one embodiment, the detachable tracking device is signaled to receive or transmit by an activation as described above. The detachable tracking device 130 may include a power switch 810 for energy efficiency. The detachable tracking device 130 also includes an indicator 132, which may be visual, such as an LED, multicolor LED, or other visual display, or auditory, such as a speaker or buzzer, or any component that sends a sensory cue.

In one embodiment, a plurality of one or more users may retrieve a plurality of one or more containers 120 at the same time using tracking devices 130 including multicolor visual indicators, with each color indicating a different customer's prescription. For example, if a plurality of one or more users requests a plurality of one or more customer's prescriptions, the prescription management system 110 sends a command to a plurality of tracking devices 130 attached to the plurality of one or more containers 120 to activate a different color for each customer. Then, the prescription management system 110 notifies the plurality of one or more users of the color associated with the requested containers 120.

In another embodiment, if a user in a plurality of one or more users is retrieving multiple prescriptions for one customer, the prescription management system 110 activates each tracking device belonging to the customer in a single LED color, allowing the user to retrieve multiple prescriptions belonging to the customer at once by selecting the tracking devices of that color. In the embodiments above, the prescription management system 110 maintains a record of the colors currently activated on at least one tracking device and selects a color to activate from colors that are not currently active.

In another embodiment, all of the prescription orders that have been sitting in the filled prescription holding area for longer than a designated holding period can be indicated at the same time by the prescription management system 110, thus allowing the user to efficiently remove aged prescription orders.

In one embodiment, if a bad batch of medication has been sent to the pharmacy, the prescription management system 110 identifies prescriptions holding the bad batch and commands the tracking devices 130 associated with the containers 120 holding the medication from the bad batch to activate the indicator signals on the associated tracking devices 130. Thus, the users can quickly remove the faulty prescription from the pharmacy.

While described with relation to a prescription management system, the prescription tracking system and methods described herein are generally applicable to tracking of any product with identifying information. For example, general product tracking and verification may be applied to other more general product tracking, such as a will-call area of a retail store, or any other situation where products are stored with tracking devices.

SUMMARY

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A system for locating customer orders, the system comprising:
    a plurality of programmable tracking devices, each programmable tracking device comprising:
        a housing for storing a product associated with the customer order, the housing coupling the programmable tracking device to the product;
        a sensor coupled to the housing, the sensor configured for sensing an open state of the housing for receiving the product and a closed state of the housing for securing the housing and the product together;
        a locking mechanism coupled to the housing, the locking mechanism configured to lock the housing in the closed state;
        a storage device, within the housing, configured for storing an order identifier associated with the customer order;
        one or more indicator sources coupled to the housing;
        a wireless interface, within the housing, configured for receiving, via a communication channel in common with the plurality of programmable tracking devices, a broadcasted order identifier associated with a desired customer order to be retrieved from a storage area; and
        a control unit, within the housing and coupled to the wireless interface and indicator sources, configured for:
            storing the order identifier associated with the customer order to the storage device, and
            responsive to receiving the broadcasted order identifier via the communication channel, determining a match between the broadcasted order identifier and the order identifier stored in the storage device, and in response to confirming the match, activating the one or more indicator sources;
        wherein a transmission of the broadcasted order identifier to the common communication channel causes, in the plurality of programmable tracking devices, activation of the one or more indicator sources for a set of programmable tracking devices that store an order identifier matching the broadcasted order identifier;
    a point-of-sale station comprising:
        a customer verification module configured to access an order identifier stored on the set of programmable tracking devices, the customer verification module further configured to determine a match between the accessed order identifier and the order identifier associated with the desired customer order; and
        a container communication module configured to read open and closed data from the sensor of the set of programmable tracking devices having one or more activated indicator sources, the container communication module further configured to send a lock or unlock command to the programmable tracking device based on the open and closed data from the sensor.

2. The system of claim 1, wherein the order identifier stored in the storage device includes prescription identifying information.

3. The system of claim 2, wherein the prescription identifying information includes an expiration date, and wherein the broadcasted order identifier indicates a threshold expiration date, and wherein the control unit is configured to activate the one or more indicator sources responsive to determining the expiration date is past the threshold expiration date.

4. The system of claim 2, wherein each programmable tracking device is configured, responsive to receiving a request to retrieve information, to transmit the prescription identifying information.

5. The system of claim 1, wherein the one or more indicator sources include a first indicator source and a second indicator source, and wherein the control unit is configured for receiving a request for the first indicator source or the second indicator source to activate and is configured to activate that indicator source in response to the request.

6. The system of claim 1, wherein the locking mechanism within the housing is configured to secure the product in a container holding the product for storage.

7. The system of claim 1, wherein the locking mechanism within the housing is configured to lock the programmable tracking device to the product.

8. The system of claim 1, wherein the housing is coupled to the product by a clip.

9. The system of claim 8, wherein the clip includes a switch to activate the programmable tracking device.

10. The system of claim 1, wherein the housing is attached to a container holding the product, and the housing is coupled to the product by being coupled to the container.

11. The system of claim 1, wherein the wireless interface is further configured to receive a programming command designating an order identifier, and the control unit is further configured to store the designated order identifier in the storage device.

12. The system of claim 1, wherein the control unit is further configured to transmit an acknowledgment via the wireless interface after confirming that the broadcasted order identifier matches the order identifier stored in the storage device associated with the customer order.

13. The system of claim 1, wherein each programmable tracking device, responsive to a user input provided to the programmable tracking device, is activated to receive the order identifier for storage in the storage device.

14. A system for locating customer orders, the system comprising:
    a plurality of containers, each container comprising:
        a bag with an open end, the open end comprising two or more sides, the bag configured for storing a product associated with the customer order;
        a handle that comprises:
            a main closure mate and a complementary closure mate, each closure mate coupled with opposing sides of the open end of the bag, wherein closing the closure mates closes the bag;
        a sensor coupled to the handle, the sensor configured for sensing an open state of the main closure mate and the complementary closure mate for receiving the product and a closed state of the main closure mate and the complementary closure mate for securing the product inside the bag;
        a locking mechanism coupled to the closure mates, the locking mechanism configured to lock the closure mates in the closed state;
        a hook attached to at least one of the main closure mate and the complementary closure mate; and
        one or more indicator sources configured to indicate the location of the container to a user; and
    a tracking device comprising:
        a wireless interface, configured for storing an order identifier associated with the customer order and further configured for receiving, via a communication channel in common with a plurality of tracking devices attached to respective containers, a broadcasted order identifier associated with a desired customer order to be retrieved from a storage area, and
        an interface connecting with the one or more indicator sources on the container, the tracking device configured to activate the indicator source responsive to receiving the broadcasted order identifier via the communication channel and confirming a match between the broadcasted order identifier and the stored order identifier, wherein a transmission of the broadcasted order identifier to the common communication channel causes, in the plurality of tracking devices, activation of the one or more indicator sources for a set of tracking devices that store an order identifier matching the broadcasted order identifier; and
    a point-of-sale station comprising:
        a customer verification module configured to access an order identifier stored on the set of tracking devices, the customer verification module further configured to determine a match between the accessed order identifier and the order identifier associated with the desired customer order; and
        a container communication module configured to read open and closed data from the sensor of the set of tracking devices having one or more activated indicator sources, the container communication module further configured to send a lock or unlock command to the locking mechanism based on the open and closed data from the sensor.

15. The system of claim 14, wherein the order identifier includes a customer identifier.

16. The system of claim 14, wherein the broadcasted order identifier includes an expiration date, and wherein the request to activate an indicator source indicates a threshold expiration date; and wherein the tracking device is configured to activate the indicator source responsive to determining the expiration date is past the threshold expiration date.

17. The system of claim 14, wherein the tracking device is configured, responsive to receiving a request to retrieve information, to transmit the stored order identifier.

18. The system of claim 14, wherein the one or more indicator sources includes a first indicator source and a second indicator source, and the request to activate the indicator source indicates the first indicator source or the second indicator source to activate.

19. The system of claim 14, wherein the tracking device is removeably attached to the container.

20. The system of claim 14, the locking mechanism is configured to lock the main closure mate and the complementary closure mate when in the closed state.

21. The system of claim 14, wherein, responsive to a user input provided to the tracking device, the tracking device is activated to receive the order identifier for storage in the storage device.

\* \* \* \* \*